US00PP14580P29

(12) United States Plant Patent
Wijnhout

(10) Patent No.: US PP14,580 P2
(45) Date of Patent: Mar. 9, 2004

(54) HEUCHERA PLANT NAMED 'PRINCE OF SILVER'

(50) Latin Name: *Heuchera sp.*
Varietal Denomination: Prince of Silver

(75) Inventor: Aart Wijnhout, Lisserbroek (NL)

(73) Assignee: Witteman + Co., Hillegom (NL)

( * ) Notice: Subject to any disclaimer, the term of this patent is extended or adjusted under 35 U.S.C. 154(b) by 0 days.

(21) Appl. No.: 10/313,117

(22) Filed: Dec. 6, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette Para
(74) *Attorney, Agent, or Firm*—C. A. Whealy

(57) ABSTRACT

A new and distinct cultivar of Heuchera plant named 'Prince of Silver', characterized by its uniformly mounded plant habit; silvery gray-colored upper leaf surfaces silvery gray with contrasting dark greenish brown-colored venation; dark purple-colored lower leaf surfaces; pink-colored flowers arranged on upright racemes; and faintly fragrant flowers.

2 Drawing Sheets

Botanical classification/cultivar designation: Heuchera sp. cultivar Prince of Silver.

BACKGROUND OF THE INVENTION

The present invention relates to a new and distinct cultivar of Heuchera plant, botanically known as Heuchera sp. and hereinafter referred to by the name 'Prince of Silver'.

The new Heuchera is a product of a planned breeding program conducted by the Inventor in Lisserbroek, The Netherlands. The objective of the breeding program is to create new Heuchera cultivars having attractive leaf and flower coloration.

The new Heuchera was discovered by the Inventor in a controlled environment in Lisserbroek, The Netherlands, from seedling progeny from a cross-pollination made by the Inventor of two unidentified Heuchera selections, not patented. The new Heuchera was selected by the Inventor on the basis of its unique leaf and flower coloration.

Asexual reproduction of the new Heuchera by cuttings taken in a controlled environment in Lisserbroek, The Netherlands, since 2001, has shown that the unique features of this new Heuchera are stable and reproduced true to type in successive generations.

SUMMARY OF THE INVENTION

The cultivar Prince of Silver has not been observed under all possible environmental conditions. The phenotype may vary somewhat with variations in environment such as temperature and light intensity without, however, any variance in genotype.

The following traits have been repeatedly observed and are determined to be the unique characteristics of 'Prince of Silver'. These characteristics in combination distinguish 'Prince of Silver' as a new and distinct cultivar of Heuchera:

1. Uniformly mounded plant habit.
2. Silvery gray-colored upper leaf surfaces with contrasting dark greenish brown-colored venation.
3. Dark purple-colored lower leaf surfaces.
4. Pink-colored flowers arranged on upright racemes.
5. Faintly fragrant flowers.

Compared to plants of the parent selections and other known selections and cultivars of Heuchera, plants of the new Heuchera differ in leaf and flower coloration.

BRIEF DESCRIPTION OF THE PHOTOGRAPHS

The accompanying colored photographs illustrate the overall appearance of the new Heuchera, showing the colors as true as it is reasonably possible to obtain in colored reproductions of this type. Colors in the photographs may differ slightly from the color values cited in the detailed botanical description which accurately describe the colors of the new Heuchera.

The photograph on the first sheet comprises a side perspective view of a typical flowering plant of 'Prince of Silver'.

The photograph at the top of the second sheet is a close-up view of a typical flowering raceme of 'Prince of Silver'.

The photograph at the bottom of the second sheet is a close-up view of typical leaves of 'Prince of Silver'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following description describe plants grown in Boskoop, The Netherlands during the late spring and early summer in an unshaded outdoor nursery and under cultural conditions which approximate commercial practice. During the period of time the photographs and description were taken, day temperatures ranged from 9 to 21° C. and night temperatures ranged from 3 to 11° C. Plants were grown as single plants in two-liter containers and were about two years old when the photographs and description were taken.

Botanical classification: Heuchera sp. cultivar Prince of Silver.

Parentage:

*Female, or seed, parent.*—Unidentified Heuchera sp. selection, not patented.

*Male, or pollen, parent.*—Unidentified Heuchera sp. selection, not patented.

Propagation:

*Type.*—By cuttings.

*Time to initiate roots.*—About 20 days at 14° C.

*Time to produce a rooted cutting.*—About 50 days at 20° C.

*Root description.*—Fleshy and well-branched.

Plant description:

*Appearance.*—Perennial; basal rosette plant habit with leaves developing from the base; full, mounded and uniform plant habit with upright racemes with pink-colored flowers. Moderately vigorous growth habit.

*Plant height.*—About 70 cm.

*Plant diameter or spread.*—About 40 cm.

*Foliage description.*—Arrangement: Basal rosette, simple. Length: About 8 cm. Width: About 8 cm. Shape: Roughly cordate; palmate. Apex: Obtuse, rounded. Base: Cordate. Margin: Crenate. Texture, upper surface: Smooth, glabrous. Texture, lower surface: Pubescence on veins. Venation pattern: Palmate, reticulate. Color: Developing leaves, upper surface: Closest to, but more purple than 197A. Developing leaves, lower surface: 187B. Fully expanded leaves, upper surface: Closest to, but more purple than 198A. Fully expanded leaves, lower surface: 187A. Venation, upper surface: Closest to, but slightly more green than N200A. Venation, lower surface: 187D. Petiole: Length: About 16.5 cm. Diameter: About 2.5 mm. Texture, upper and lower surfaces: Smooth, glabrous. Color, upper and lower surfaces: 187B.

Flower description:

*Appearance/arrangement.*—Single campanulate flowers arranged on numerous upright racemes; about 40 flowers and flower buds per flowering stem. Flowers face outward to slightly upright. Flowering continuous with about eight flowering stems per plant developing throughout the flowering period. Flowers not persistent.

*Fragrance.*—Faint, sweet and pleasant.

*Time of flowering.*—Under natural conditions, plants flower from late April to late June in The Netherlands.

*Flower longevity.*—Flowers last about one week on the plant.

*Inflorescence height.*—About 20 cm.

*Inflorescence diameter.*—About 2.3 cm.

*Flower size.*—Diameter: About 4 mm. Depth (height): About 6 mm.

*Flower buds.*—Height: About 3 mm. Diameter: About 2 mm. Shape: Ovoid. Color: 151C; towards the base, 64B.

*Sepals.*—Quantity/arrangement: Five sepals; radially symmetrical and fused at base. Length: About 6 mm. Width: About 2 mm. Shape: Oblong. Apex: Obtuse. Margin: Entire. Texture: Densely pubescent. Color: When opening, upper surface: 64C to 64D; towards the margins, lighter than 64D. When opening, lower surface: 65C; towards the margins, lighter than 65C. Fully opened, upper surface: 64D; towards the margins, lighter than 64D. Fully opened, lower surface: 65D; towards the margins, lighter than 65D.

*Petals.*—Quantity/arrangement: Five minute petals; radially symmetrical. Length: About 4 mm. Width: About 1 mm. Shape: Narrowly oblanceolate. Apex: Acute. Margin: Entire. Texture, upper and lower surfaces: Smooth, glabrous. Color, when opening and fully opened, upper and lower surfaces: Closest to 155D.

*Peduncle.*—Strength: Strong; flexible. Aspect: Upright. Length: About 70 cm. Diameter: About 3 mm. Texture: Densely pubescent. Color: 200A to 200B.

*Pedicels.*—Strength: Moderately strong to strong; wiry. Aspect: About 30 to 50° from vertical. Length: About 1 cm. Diameter: About 0.75 mm. Texture: Pubescent. Color: 200A.

*Reproductive organs.*—Androecium: Stamen number: Five per flower. Anther shape: Oblong. Anther length: About 0.6 mm. Anther color: 171A. Amount of pollen: Little to none. Gynoecium: Pistil number: Two per flower. Pistil length: About 4 mm. Stigma shape: Club-shaped. Stigma color: 158B. Style length: About 3 mm. Style color: 158B. Ovary color: 158A.

*Seed/fruit.*—Seed and/or fruit production has not been observed.

Disease/pest resistance: Resistance to pathogens and pests common to Heuchera has not been observed on plants grown under commercial conditions.

Temperature tolerance: Plants of the new Heuchera have demonstrated good tolerance to night temperatures as low as −12° C. and day temperatures as high as 30° C.

It is claimed:

1. A new and distinct cultivar of Heuchera plant named 'Prince of Silver', as illustrated and described.

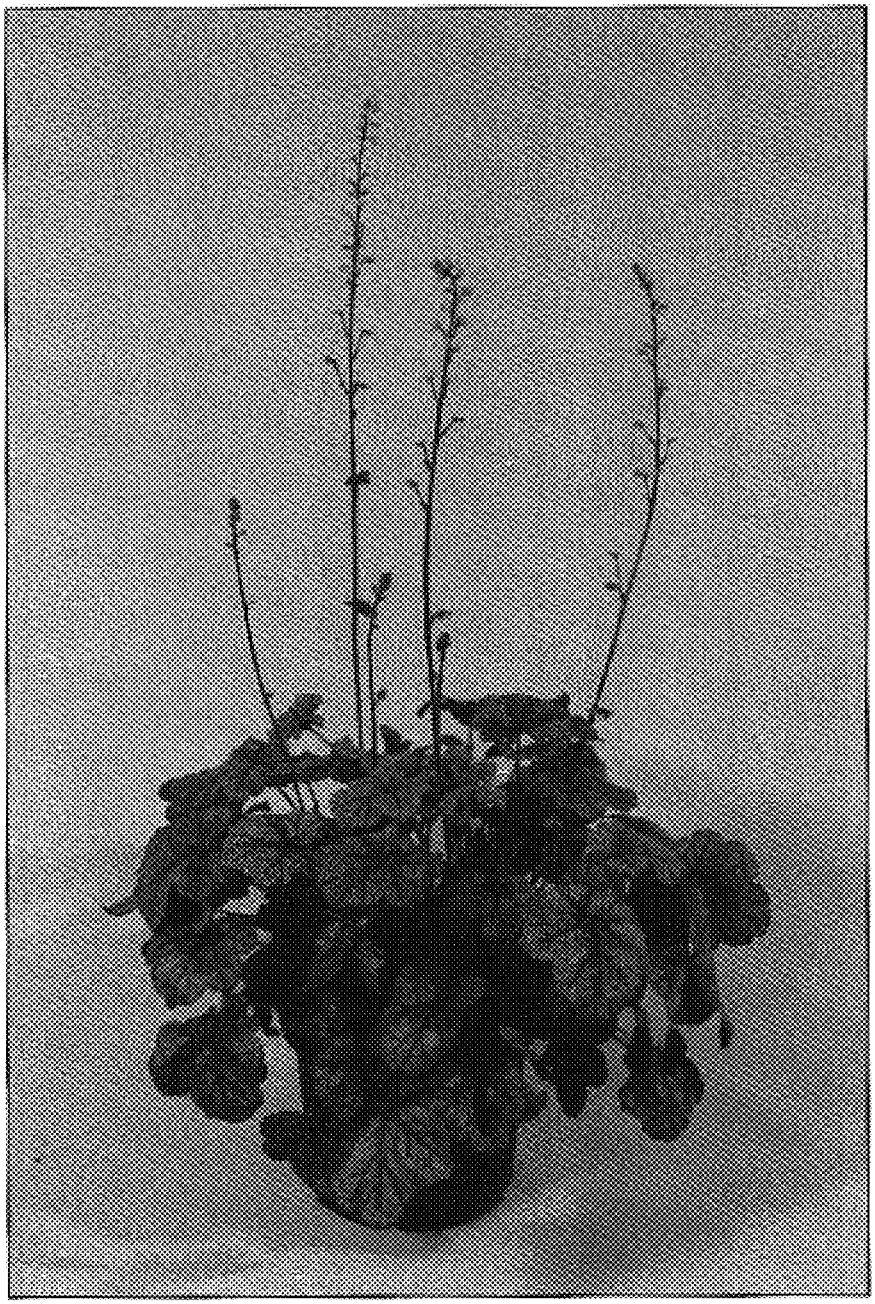

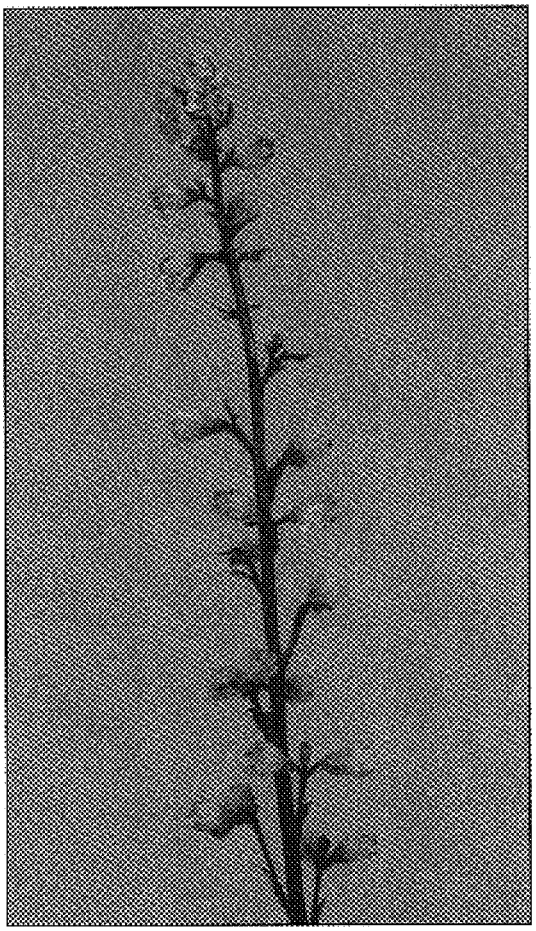
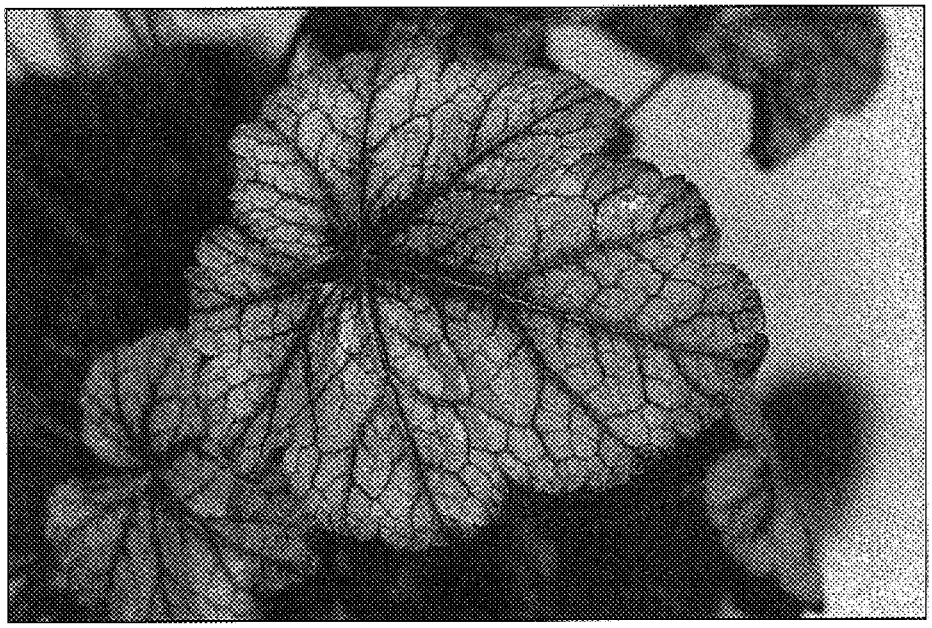

* * * * *